(12) United States Patent
Graham et al.

(10) Patent No.: US 9,766,256 B2
(45) Date of Patent: Sep. 19, 2017

(54) MAGNETIC PARTICLE TAGGED REAGENTS AND TECHNIQUES

(71) Applicants: Henry A. Graham, Solana Beach, CA (US); John G. Gorman, Del Mar, CA (US); James P. Rowell, Stockton, NJ (US)

(72) Inventors: Henry A. Graham, Solana Beach, CA (US); John G. Gorman, Del Mar, CA (US); James P. Rowell, Stockton, NJ (US)

(73) Assignee: CHROME RED TECHNOLOGIES, LLC, Stockton, NJ (US)

( * ) Notice: Subject to any disclaimer, the term of this patent is extended or adjusted under 35 U.S.C. 154(b) by 0 days.

(21) Appl. No.: 15/330,443

(22) Filed: Sep. 22, 2016

(65) Prior Publication Data

US 2017/0016922 A1   Jan. 19, 2017

Related U.S. Application Data

(63) Continuation of application No. 11/715,411, filed on Mar. 8, 2007, now Pat. No. 9,488,665, which is a continuation-in-part of application No. 11/518,189, filed on Sep. 11, 2006, now abandoned.

(60) Provisional application No. 60/716,591, filed on Sep. 13, 2005.

(51) Int. Cl.
*G01N 33/80* (2006.01)

(52) U.S. Cl.
CPC ......... *G01N 33/80* (2013.01); *G01N 2446/00* (2013.01)

(58) Field of Classification Search
CPC ............................ G01N 33/80; G01N 2445/00
USPC ........................................................ 436/526
See application file for complete search history.

(56) References Cited

U.S. PATENT DOCUMENTS

| 4,672,040 A | * | 6/1987 | Josephson | .......... B01D 15/1807 |
| | | | | 252/62.51 R |
| 4,868,130 A | * | 9/1989 | Hargreaves | ............. B01L 3/502 |
| | | | | 435/7.7 |

* cited by examiner

*Primary Examiner* — Mark Shibuya
*Assistant Examiner* — Nam Nguyen
(74) *Attorney, Agent, or Firm* — Ralph T. Lilore

(57) ABSTRACT

Methods for separating, cells, particles, or other molecules of interest (MOI) from unwanted materials not of interest (MNOI). by forced movement of MOI into certain zones having properties which deter the entry of unwanted materials. MOI are tagged with magnetic particles and moved with a magnetic field through a fluid, or zones, of higher specific gravity that prevents, unwanted less dense materials from entering. Buoyant or other forces are used to remove any unbound material from the complexes with ASG before reading. Readable labels include the magnetic particle tagged complex itself, and other labels such as enzymes, chemiluminescent materials, radioactive isotopes, chromogenic and fluorogenic substrates and other labels may be used. The invention applies to many assays, diagnostic tests, separative procedures and chemical syntheses.

20 Claims, No Drawings

US 9,766,256 B2

MAGNETIC PARTICLE TAGGED REAGENTS AND TECHNIQUES

CROSS REFERENCE TO RELATED APPLICATIONS

This application is a continuation of U.S. application Ser. No. 11/715,411 filed Mar. 8, 2007 which in turn is a continuation-in-part of U.S. application Ser. No. 11/518,189 filed Sep. 11, 2006, which claims the benefit of U.S. Provisional Application 60/716,591, filed Sep. 13, 2005.

STATEMENT REGARDING FEDERALLY SPONSORED RESEARCH OR DEVELOPMENT (Not Applicable)

REFERENCE TO A SEQUENCE LISTING, A TABLE, OR A COMPUTER PROGRAM LISTING APPENDIX SUBMITTED ON COMPACT DISC (SEE 37 CFR 1.52(e)(5))

(Not Applicable)

FIELD OF THE INVENTION

This invention relates to a method for separating cells, particles, and molecules or analytes, unreacted reagents, and other materials of interest from associated or contaminating material or unwanted material such as proteins, for use in many assays, diagnostic procedures, and preparative processes.

More particularly, it relates to performing the above procedures by a novel method whereby cells, particles, molecules, analytes or other materials of interest are separated from a liquid mixture or surface containing contaminating or interfering materials by a novel process utilizing buoyant forces with reactive magnetic particles and liquids of selected specific gravity and magnetic forces.

The invention also relates to cell separations and microscopy, immunoassays, chemical synthesis, molecular separations and particularly to blood bank diagnostics as well as many other scientific procedures and industrial manufacturing and quality control processes, wherein magnetic particles and magnetic forces are used to effect the separation in a liquid medium.

This invention further relates to new and improved in vitro diagnostics (IVDs) assays which can detect disease at the molecular level i.e., chemical and biological assays, including nucleic acid based assays (molecular diagnostics).

The invention also relates to chemical synthesis procedures that utilize a sequential process where products of a reaction are built up through a series of addition and removal steps to produce a final product, additions of amino acids or synthesis of nucleic acid polymers, and the removal of reaction products not bound to the movable particle or surface.

It further relates to determination of antigens, antibodies and other proteins on blood cells, in blood serum and other bodily samples and the use of buffers and other liquids in the determination process.

The invention further relates to blood banking immunological diagnostic testing and immunohematology and more particularly to blood cell serological testing using magnetic particles and magnets to separate bound entities to be measured from unbound entities.

It further relates to determination of antigens, antibodies and other proteins on blood cells, in serum and other bodily samples and the use of buffers and other liquids in the determination process.

It further relates to cell separation procedures common in cancer research, diagnostics and therapy, and in flowcytometer and cell sorter applications for counting or harvesting particular cell types.

BACKGROUND OF THE INVENTION

General Background

Clinical and industrial laboratories and chemical manufacturing plants represent an enormous, widespread industry in which many procedures and processes require, or are significantly enhanced by, separation of a known or unknown material of interest from materials in the process which are not of interest, and which may interfere with the good performance of the process.

Many of these procedures are assays performed to determine the amount of a given entity in a sample which is present along with many other entities. In the health and medical sectors, this includes, for example, the isolation, expansion and identification of genetic material, usually from body liquids or tissues, as well as the detection and quantification of antigens, antibodies, and other proteins and small molecules. On the environmental level it is desirable to determine the amount or presence of materials in water, air, chemicals, foods and the like.

Modern-day immunoassays are a good example of the many and varied laboratory and manufacturing procedures and processes that require purification of a material by separation from contaminants and other materials. Immunoassays in which small amounts of an analyte are sought and measured in a sample, have evolved from the early, generally chemical, formats of various kinds of techniques. Binding partners, either specific for a given epitope or polyclonal in nature, have been employed in reaction with the desired target (be it known or unknown) to produce an entity which can be detected through a label attached to it or through some discernable, measurable effect upon a component of the test or on a substrate reactable with the label. Generally speaking, most, of the commercially useful versions of such tests require that the reacted binding partner be separated from unreacted binding partner so as to determine whether the sought entity has reacted or not reacted and how much is present.

The need to separate reactants from interfering substances is a major design feature in immunoassays, blood bank procedures, and chemical synthesis procedures. Many variations on several separation or washing techniques have been utilized, often involving dilution with large quantities of wash solution or sample, and often presenting the element of the test which determines the ease, complexity, cost, overall time, and sensitivity of the test, as well as the design of automated assay systems and the volume of hazardous material to be controlled and discarded. Immunoassays typically use both dilution and decanting or lateral liquid flow on chromatographic membrane or paper strip, with large quantities of diluent or sample as washing methods. If a convenient separation method could be made available, alternative methods would be more readily adopted. An appropriate alternative separation concept would be broadly useful for immunoassays, including the special case of immunoassays that are utilized in blood banking involving cellular antigens and antibodies to them, and sequential chemical synthetic procedures.

Dilution And Decant Wash Methods

Historically, the most common wash method in immunoassays, involves the immobilization of a reagent antibody on a portion of the surface of individually coated containers, such as a microtiter well or test tube, then washing away undesired material by repeated wash solution additions and decanting steps. When this method is used, the final reaction is observed in the same tube or well that was washed with the possibility that any contaminating material attached to its sides or inadvertently remaining in the container would interfere with the specificity or sensitivity of the assay. Additionally, the discarded liquids are often contaminated with hazardous material. Similar problems are encountered when the assay is done on a chromatographic paper strip.

Microsphere and Particle Methods for Separation

In many laboratory methods the material of interest is specifically captured on particles or microspheres as the solid state surface. Such particles or microspheres are employed in many and varied diagnostic and preparative methods. Their primary purpose in these methods is to separate or purify specific items of interest from unwanted surrounding contaminating materials. Similarly, in blood bank red cell testing the red cell itself is the particle surface that captures material of interest. The active binding agents affixing such particles include antibodies, ligands, lectins, oligonucleotides and many other specific binding molecules of non-immune origin. Methods are well known and commonly practiced which enable the preparation of particles and microspheres of various size, specific gravity, and other properties to be attached to reagents which can specifically bind to specific cells, viruses and sub-cellular particles or other materials of interest.

When particles of various kinds are bound to materials of interest, they become much larger complexes which settle more rapidly under Stokes law. Larger denser complexes can be sedimented or centrifuged from a mixture and thus washed. Unfortunately this method requires centrifugation to create force to move the particles, and the medium must have a lesser specific gravity than the particles which restricts media that can be used and limits the power of the separation.

Variations of the dilution/decant wash systems are common. Many use a single coated bead, or coated micro particles in the test tube which typically must be centrifuged prior to every decanting. Segregation of materials with magnetic particles bound to a ligand or antibody that selectively binds to an entity of interest is in wide use for purposes of separation or segregation. However, these methods usually require fixation on a surface and physical washing by flow of washing liquid requiring decanting or control of liquid flow with pumps and valves, adding considerable complexity to automated instruments and mechanical and robotic systems. Thus, when coated magnetic particles are used, the application of a magnet to the side of the tube before each decanting step is required.

Magnetic Particle Wash Methods

Some current separation methods use, as an alternative to centrifugation, separation by a process in which magnetic particles are bound specifically to the materials of interest to form a complex which is then selectively separated from materials not of interest by the pull of a magnetic field rather than by centrifugation or by gravity alone. Usually the material to be separated is pulled to the side of the vessel by magnetic force and the material not of interest removed by decanting or rinsing or other liquid flow past the material of interest held on the wall.

Lateral Flow Wash Methods

A current art-preferred method of conducting a wide variety of assays involves the use of individually coated chromatographic strips whereby a sample suspected of containing the analyte sought to be determined is applied either alone, or with appropriate reagents, to a chromatographic membrane or layers of membranes and allowed by lateral flow to come into contact on the strip with previously immobilized materials. Depending on the nature of reactants chosen, the immobilized reagents act to separate the desired test components so that a proper determination of the presence of the analyte can be made. This procedure typically passes the sample and labeled reagents laterally along a chromatographic strip and into the binding zone to bind with an immobilized reagent. Non-specific binding material to the immobilized reagent or to the strip is to be avoided or eliminated and therefore sufficient wash liquid must pass through the zone to remove unbound material.

While, in general, lateral flow methods have the advantage of eliminating centrifugation steps and much of the liquid handling steps required for washing reactants in other methods, many lateral flow methods involve reagent addition steps during the procedure. For example, Becton Dickinson ColorPac® lateral flow devices may require pipetting of as many as six reagents during an analytic procedure.

An alternative chromatographic strip technology has been described in U.S. Pat. Nos. 6,713,271 and 6,136,549 assigned to Wavesense LLC of Laguna Beach, Calif. In these two patents, magnetic assay methods and systems are described in which uniform bulk-prepared microparticle reagents and liquid reagents are substituted for the immobilized materials commonly used on the strip. Instead, magnetic particle-tagged reagents participating in the test and flowing on the strip are captured and held at a desired site on the strip by a magnet field applied to the site. The captured particles are read to determine the presence or absence of the analyte sought. Large volumes of wash liquid are required to move sample and unbound reactants away from the observation zone.

Density Gradient Wash Methods

Density gradient separation is a commonly used separation method that employs a density gradient column and centrifugation. Density gradient separation methods separate materials of a mixture based upon their density. Materials of different density will spin down under centrifugation until they reach a liquid media layer of equal specific gravity. They "float" and do not enter the regions of density equal or higher than their own.

Separation based on the rate of sedimentation of particles through a density gradient to separate them from materials with a lower specific gravity that will either float on the density gradient or move to a different layer in the gradient or sediment at a slower rate than the larger particles has been used for blood bank serological testing. In this method, cells are forced by centrifugal force through a solution of intermediate density which allows the heavier red blood cells to pass through and floats the less dense serum on the top. The washed red cells can either be recovered following a decant step or be assayed in place by incorporation of a reagent into the solution of intermediate density, eliminating the need for a decant step.

Sequential Chemical Synthesis Background

Industrial chemical synthetic procedures often require the removal of reactive materials prior to the sequential addition of the next reactant, and then the removal of that reactant prior to the addition of the next reactant. Thus, separation and wash procedures play a major part of determining the physical manipulations required in a synthetic process.

Blood Transfusion Background

Blood Banks collect more than 15 million units of blood annually for more than 14 million transfusions in the United States. Pretransfusion testing of patient and donor blood samples is an enormous industry distributed over nearly 10,000 large and small blood bank laboratories.

Blood Banks test to determine the blood type of red blood cells of donors and patients, to detect antibodies in blood sera, and perform compatibility (crossmatch) tests and for potential infectious disease agents in every donor blood sample.

The following blood bank tests are among the most important and most frequently conducted tests:
1—Direct red cell antigen testing, typically ABO grouping and Rh typing
2—Reverse grouping (testing for antibodies in serum which react with A or B cells)
3—Antiglobulin based tests which require a serum protein removal step as a part of the procedure. These include indirect typing procedures for antigens (such as Kell, Duffy, Kidd and some Rh procedures), direct antiglobulin test (test for serum proteins on an individuals' red cells), indirect antiglobulin tests (includes antibody screening, antibody identification and the crossmatch).

The following is a description of common blood bank reagents and techniques.

Blood Bank Reagents and Techniques

THE DIRECT COOMBS (Antiglobulin) TEST: The direct Coombs (antiglobulin) test, which is used in the investigation of anemias, will demonstrate whether red blood cells are coated with incomplete antibody, especially that of babies born to Rh-negative mothers. It will reveal whether antibodies have been adsorbed on the surface of the red cells while the baby was in the uterus and is important in diagnosing Rh hemolytic disease of the newborn. The direct Coombs (antiglobulin) test is performed by washing the red blood cells to be tested and attempting to agglutinate them with Coombs (antiglobulin) reagent. The Coombs reagent is widely available. This test, as well as the indirect test described below, are variously referred to herein as Coombs test, anti-globulin test, AHG test or variations thereof. The serum is variously referred to as Coombs serum, anti-human globulin serum, AHG serum or the like.

THE INDIRECT COOMBS (Antiglobulin) TEST: The indirect Coombs (antiglobulin) test is used to screen the patient's serum for atypical antibodies such as Rho (D), Kell (K), Duffy (Fya), and hr' (c). The presence of any of these atypical antibodies can cause hemolytic disease of the newborn or transfusion reactions.

In the indirect test, an unknown serum is tested with human group O reagent red blood cells. Group O reagent antibody screening cells are available commercially. They are a group of two or three O Rh positive and Rh negative donor red blood cells selected so as to be positive on at least 50% of the cells for each of the common clinically important red blood cell antigens. If a serum gives a positive reaction with such screening cells, tested separately or as a mixture, it must contain an atypical antibody of unknown identity. The techniques involved in performing the direct and indirect antiglobulin and the reasons therefore, are well-known in the art.

ABO GROUPING: Red cell (forward) typing with anti-A or anti-B reagents will demonstrate the presence or absence of A and B antigens on the red cell. Serum (reverse) typing with reagent A and B red cells will demonstrate the presence of anti-A and anti-B in the serum.

OTHER REAGENTS USEFUL IN ABO GROUPING: Other reagents may be used routinely in ABO grouping. They are often essential for resolving discrepancies between forward and reverse typing. Blood is not usually released from the blood bank for transfusion until any such discrepancies have been resolved. Anti-A, B (Group O serum) can detect weak A variants that may be missed by regular anti-A reagent. Other reagents: Anti-A, B reagent (Group O serum), Anti-$A_1$ reagent (absorbed B serum or Dolichos lectin), Anti-H lectin (Ulex), Reagent O Rh-positive screening cells, Reagent $A_2$ cells.

COMPATIBILITY TESTING: Crossmatch (compatibility) tests are performed to determine the suitability of the donor's blood for the particular recipient. Blood transfusions are not given before performing a major crossmatch to test the donor's red cells against the serum of the recipient. If both donor and recipient are of the same blood group, a minor cross-match may be done to test the recipient's red cells against the donor's serum. The minor crossmatch is of no value when donor and recipient belong to different blood groups because agglutination will occur. Major Crossmatch involves mixing donor's red cells with recipient's serum, centrifuging at 37° C. and adding antiglobulin reagent. Minor Crossmatch involves mixing donor's serum with recipient's red cells, centrifuging at 37° C. and adding antiglobulin reagent.

RH TYPING: The crossmatch makes it possible to avoid hemolytic transfusion reactions following a particular transfusion. Blood banks are also concerned about isosensitization. If, for example, a blood bank selects Rho (D)-positive blood for an Rho (D)-negative woman, she will not have an incompatible crossmatch or a transfusion reaction if she has no anti-Rho (D) antibodies in her blood, but she may become sensitized to the Rho (D) antigen. Initiation of the immune response presents problems for subsequent transfusions and for subsequent pregnancies if she has an Rho (D)-positive mate. Rho (D) negative donors, Rho (D)-negative women and their Rho (D)-negative mates, and Rho (D)-negative cord bloods are tested for the presence of Rho\variant (DU) antigen that may not always be detected by the anti-Rho (D) slide test. Various Rh typing methods and the appropriate controls are well-known to the art.

ANTIBODY TESTS: Screening for antibodies is especially important for patients receiving blood and the obstetrical patient. In obstetrical patients, early detection allows time to prepare for possible intrauterine or exchange transfusion in cases of Rh hemolytic disease of the newborn. Once the presence of an antibody has been detected, the problem of its identification remains, but this has been simplified by the development of antibody identification panels of group O reagent red cells. These screening and identification methods are well known to those skilled in the art.

Most blood bank tests require a wash step during the procedure. The centrifugal washing step, either by dilution and decant or sedimentation into beads or gel takes about 5 to 10 minutes. The indirect antiglobulin test (IAT) is the most used and most reliable test in blood banking to determine binding of antibodies to red blood cells. This test is performed manually in test tube, requires addition of red cells and antisera, three manual centrifugation and decanting steps and finally a careful evaluation under the microscope by a skilled technologist of whether the red cells have agglutinated, and recording of results. It is very labor intensive.

Although red cells in the presence of appropriate antibodies may clump in the absence of centrifugal forces, centrifugal procedures are typically used for almost all blood bank serological assays to cause enhanced aggregation of red cells for naked eye visualization at the assay end point. This is a major cause of a need to repeat an assay.

Classically, blood bank methods for determining blood types or detecting red cell antibodies in donor or patient sera are done manually in a large percentage of blood banks and rely upon hemagglutination as the endpoint to determining whether red cell antibodies have reacted with red blood cells in donor or patient blood samples.

Blood bank testing procedures have historically been a somewhat special case in the immunosassay art because the red blood cell, which is not visible to the naked eye, can form small aggregates that are visible to the naked eye and have a pattern distinguishable from that of nonaggregated red blood cells. Thus the typical blood bank procedure relies on human pattern recognition to detect a reaction. In blood bank testing, a wide variety of tests are performed using classical, traditional wet chemistry techniques.

In recent years the manual DiaMed-ID (D-ID) antiglobulin gel test (Ortho Clinical Diagnostics, Raritan, NJ) has largely replaced the classical manual method. It requires a ten minute centrifugation step and a more straightforward manual reading.

More and more testing is now being performed on automated instruments. For example, the Ortho Pro-vue (Ortho Clinical Diagnostics, Raritan, N.J.) is an automatic gel technology system, while the ABS200 and Galileo instruments (Immucor, Norcross, Ga.) and the Olympus Tango and Olympus PK700 blood center instruments (Olympus, Mellville, N.Y.) are other large volume systems. All three instruments require centrifugation.

There are other blood bank laboratory and forensic laboratory applications where it is important to detect the presence of a minor population of red blood cells from a second individual in a sample of blood belonging to the first individual, such as athlete blood doping.

This test is valuable in assaying the survival of transfused blood from various donors, as a biological compatibility test, multiplexing cross-matching of many donors with a patient(s) in one reaction vessel, antibody screening with multiple cells, research investigation of rare red blood cell chimeras and other special situations, in addition to detecting fetal red blood cells in a sample of maternal blood from an Rh Negative mother.

Fetal Maternal Hemorrhage Background. One special case for use of the invention in a blood bank laboratory is the test to detect Fetal Maternal Hemorrhage (FMH) in pregnant Rh negative mothers. This test has become very important in the field of perinatal medicine and test methods currently available are far from ideal. The invention can be readily adapted to detect and quantitate fetal red cells in blood samples from Rh-negative mothers and do so in a superior manner.

During pregnancy the blood circulations of mother and baby are separate and do not mix. However, some leakage of small amounts of blood from the baby's circulation into the mother's circulation is usual in almost every pregnancy and is known as Fetal Maternal Hemorrhage (FMH). Diagnostic tests to detect and measure the amount of baby's blood in the mother's blood sample are very important in the case of an Rh negative mother pregnant with an Rh positive baby. In these cases RBC leakage from an Rh positive fetus to an Rh negative mother, i.e., fetal maternal hemorrhage (FMH) occurs late in pregnancy and during delivery may cause Rh immunization of the mother. This will cause consequent Hemolytic Disease of the Fetus and Newborn in her future Rh-positive babies. It is thus, very important to screen for and detect such occurrences.

The current screening test is a commercially available kit which employs mixed field detection in which any baby's red blood cells in the mother's blood sample form "rosettes" which are seen under the microscope and counted by a technologist.

The currently used quantitative test for fetal red blood cells in mother's blood, the Kleihauer-Betke fetal cells stain and manual count, is used when the screening test is positive. It is sensitive to less than 0.1 ml of fetal cells in the mother's circulation and is quantitative. However, the Kleihauer-Betke test is not entirely satisfactory since because it is manual, time consuming, requires skill and care, involves a technician training and competency assessment, uses unstable unpredictable reagents, is prone to false positive and false negative results and is very imprecise.

There is thus, an unmet need for a FMH test that is rapid, economic and performs both screening and quantitative functions, and is objective in that it gives a numeric result free from the subjectivity of the technologist's interpretation or rosette counts in a microscopic field.

SUMMARY OF THE INVENTION

The invention comprises reagents and methods for separation of materials of interest from materials which would interfere with the test from other contaminating materials not of interest called collectively herein MNOI or materials not of interest, in a continuous fluid medium through the forced movement of materials of interest through at least one fluid zone but preferably a multizone liquid medium into certain zones, which have specific gravity and other properties selected to deter the entry of unwanted materials. Materials of interest, in the movable complex, are forced into contact with a reactive surface capable of binding the material of interest and holding it to the surface. When the initial movement force is removed, a second opposing buoyant force causes the removal of the unbound material from the surface by floatation. Following the floatation removal of unbound material, the reactive surface is observed for the complexed material of interest.

The invention can be described generally as the use of:
1. magnetic particles attached to a binding partner (Mag.BP) of usually a Material of Interest (MOI).
2. a reaction of the Mag.BP particle reagent with the MOI
3. a force, such as a magnetic field for moving reacted MOI.
4. a movement of MOI from a zone or through multiple zones in a continuous liquid medium, 5. specific capture of MOI on a surface
6. an application of a counterforce, such as flotation by removal of the magnetic force, or the application of an additional magnetic field in the opposite direction.

The term magnetic is also meant herein to include paramagnetic. The preferred method of the invention employs a magnetic field as the moving force. The buoyancy effect on the MNOI or interfering materials is caused by their natural tendency to float on the underlying, more dense layers. The objective is to move only the materials of interest complex into one zone where they may be read or measured and leave interfering materials floating in a different zone where they will not alter the reading step. This preferred method of forcing differential movement of complexed materials of interest, but not of materials not of interest is by tagging the MOI with magnetic particles bound to an MOI binding partner and directing their movement with a magnetic field through one or more contiguous layered fluid zones with higher specific gravity. Flotation of lighter materials prevents unwanted materials from entering denser zones onto which the magnetic field forces MOI Preferably, zones are layered and remain layered on the basis of non-miscibility and specific gravity, and materials of interest are subjected to the force by the presence of the magnetic particles. They are moved through the zones by the force of a magnetic field. Thus, it can be seen that the magnetic particles are attached to a key reactant which binds to the MOI, or to a material (a cell for example) that can bind to the MOI.

Some of these delivery destination areas may have specific capture mechanisms, such as surface attached antibodies or other ligands which bind the MOI. after the magnetic field is removed. Other embodiments of capture make use of the properties release after the magnetic field is removed. Controlled gentle consistent release may be obtained by thus applying a flotation counterforce, by utilizing a layer of greater density than the complex as the last fluid zone or introduction of a dense layer into the vessel at read time, which will sink to the bottom and float off any material not actively bound to the floor, leaving the bound material alone to provide a clean signal.

The invention contemplates a new series of reagents which function in a liquid medium. In particular, the specific gravity of the magnetic particles and the separating zone are matched so that the magnetic particles alone or complexed have a lower specific gravity than the separating zone adjacent to the capture binding surface. This assures that the particles and complex will stay in suspension in a zone layer with a matching specific gravity and will not sediment out of that layer, without the application of magnetic force. Application of a magnetic force to the MOI complex to move it to the binding surface, and the subsequent removal of the magnetic force after they have been deposited on the surface will result in the separation by flotation of any that are, not specifically bound by the MOI—binding surface complex.

The zones may contain appropriate reactants which cause chemical or physical processes to occur before materials are moved on into the next fluid zone. The invention is characterized generally by moving the particles through the liquid media rather than flowing liquids over the particles.

The invention applicable to many scientific, clinical and industrial areas including in vitro diagnostic (IVD) testing including blood bank pretransfusion testing, cell separation, microscopy, chemical synthesis in many fields from cancer research and diagnosis to chemical manufacturing.

Importantly, the invention simplifies nearly all of the scientific, clinical and industrial procedures and processes that require separation and purification of materials of interest from contaminating or interfering materials not of interest. Simplification comes largely from the elimination of centrifugation as a necessary step in the prior art and elimination of the need for fluid handling required for washing away contaminants, including reservoirs, pumps, tubing, valves and electronic controls that currently complicate instrument and equipment systems currently used in such procedures and processes.

The present invention is useful in performing virtually all tests that are performed in the blood bank winch Involve reactions between binding partners, such as immunological binding partners or universal binding partners such as lectins, biotin-avidin, Protein A or G, ligands and their receptors and the like. As so applied, magnets and magnetic particle-labeled reagents are used to capture and/or release magnetic particle-tagged entities for immunohematology diagnostic testing purposes. The magnetic tagged entities may be, depending on the particular assay, any of tagged antibodies, tagged blood cells, tagged universal binding partners, especially rod blood cells, binding agents such as lectins, biotin-avidin, Protein A or G, ligands and their receptors and the like.

In this aspect, the invention utilizes magnetic particles directly labeled with antibody (such as anti-A, anti-B, anti-D or anti-human serum). With such reagents used in the assays of the invention, the red cells will only react with magnetic particles if the red cells have the reactive antigen corresponding to the specific antibody on the particles (and in the case of anti-human serum, have been washed clean of serum). In these assays, the presence of an RBC on a magnet, is a positive event for the presence of the antigen sought and can be seen because of the hemoglobin in the cells.

Another reagent used in the invention are magnetic particles labeled with a red cell binding partner, i.e., a lectin or other universal red blood cell binding material (in effect an anti-RBC). The lectin or other binding molecule should be able to bind magnetic particles to all human red blood cells regardless of blood group, and must not react with Coombs serum or other human antibodies. The magnetic particles are used to move the RBCs through zones or are positioned at a location on a chromatographic strip so that fluids can move by the cells (i.e., the fluids move over the comparatively stationary cells). In this more universal format, a labeled AHG reagent, not bound to a magnet, but labeled with a detectable indicator such as an enzyme, fluorophor, and the like, described in more detail below, is used to react with the magnet bound red cell complex and any bound serum antibody.

The invention also may employ software to sense the progress of the process to provide feedback to timing of incubation, reagent dispensing, order, amount of reagent dispensing, application or removal of magnetic field and the like.

The invention is not restricted to magnetic field forces and flotation counterforces. Other types of forces are employed in other embodiments. For example, sedimentation under gravity or centrifugation or electrophoresis or simply depending on the natural properties of the materials and fluid zones, such as density may be used to achieve separation. Thus, the invention envisages many variations on the general method of differential entry of MOI and MNOI into and through zones in a continuous fluid medium. Such variant methods may, among others, alter the relative strengths of force and counterforce by varying the strength and direction of magnetic fields by varying the size of magnetic particles, by varying flotation force, by varying the specific gravity of fluid zones and employing and/or several different color labels to tag several MOI in a separated subset. One particular class of magnetic reagent is a magnetic particle tagged with a very light flotation moiety. This class of mag-reagent is able to form a mag.antibody.analyte complex of specific gravity less than 1.0, allowing the sample itself to act as the repugnant dense layer. It is apparent to one skilled in the state of the art that magnetic particles can be made floatable in aqueous solutions by coating them with polystyrene microspheres. The preferred forces of the invention however are the magnetic field to move the magnetic particles and flotation as by removal of the magnetic field to separation MNOI. The intensity, direction and timing of the magnetic fields may change as suited to the steps of the procedure.

The invention envisages a new series of fluids employed in novel layers to obtain the necessary properties to exclude entry of unwanted materials including non-miscibility, specific gravity, chemical reactivity or inertness. These will be required by the various methods, procedures and processes now made possible by the invention.

Readable labels such as enzymes, fluorophors, chemiluminescent materials, radioactive isotopes, and other labels may be attached to materials of interest and they may be delivered to a final zone for reading or harvesting. Such reagents may be preintroduced into appropriate zones during test kit manufacture so they will react only when materials of interest traverse that reagent zone.

The invention includes delivery of selected materials of interest to a reading zone where they may be detected and measured. They may also be delivered to a harvest area where highly purified materials may be collected for further use. In the case of cells, they may be delivered to a microscopic slide to other surface for counting, staining and microscopic examination, to cell media for cell culture, or for molecular studies such as PCR.

DETAILED DESCRIPTION OF THE INVENTION

The invention comprises unique novel reagents and methods for separation of materials of interest from interfering materials or contaminating materials not of interest in a continuous single or multizone liquid medium. For example, in many industrial and laboratory procedures, such as assays or chemical syntheses, it is necessary to separate reactants from non-reactants especially when the separation is beneficial or necessary for the success of subsequent assay steps. For this purpose, separation of reactants from non-reactants or interfering substances, the invention utilizes the forced movement of selected materials through different zones of a continuous single or multizone liquid medium where only certain desired materials of interest are caused to move into or through the zone or zones. Depending on the particular assay or procedure being performed, the materials not of interest need not necessarily be separated if their presence does not interfere with the quantitative or quality measurement of the material of interest.

The invention utilizes a vessel or an array of vessels such as a microtiter plate containing a continuous liquid medium which is divided or layered into at least one but preferably more than one discrete liquid zones with different physical or chemical properties. The invention is based upon forced movement of selected particles through this continuous but multizone liquid medium. The zones or layers of the liquid medium are designed chemically and or physically to reject or significantly retard, entry of materials not subject to the force, or to apply a counterforce to MNOI. On the other hand, materials of interest, rendered subject to the force, can be forced to enter and pass through certain zones that they would not normally enter, or that they would be retarded from entering. In certain cases, the force will overcome any counterforce that applies to MOI. In this manner MOI can be isolated and purified of all contaminants and delivered to a reading or harvest zone.

The method specifically takes advantage of:
1. a purposefully designed zone or multiple zones, in a continuous liquid medium
2. magnetic particles,
3. a magnetic field force
4. a buoyant force
5. a capture surface.

There are many and varied assay formats which may be used to take advantage of the present invention. Following are some general methods.

In the preferred embodiment, zones are layered and remain layered on the basis of one or more of poor or non-miscibility, differing viscosities or surface tensions, hydrophobicity, hydrophyllicity and specific gravities. The materials of interest are treated with a binding partner to which magnetic particles are bound and then moved as a reacted complex through the zones by the force of a magnetic field. In many cases, materials of interest, even when complexed can be forced into zones of density greater than that of the materials themselves, i.e. zones in which they would not have entered but for the application of a selective force.

The inventive methods are applied to immunoassays in general, to virtually all blood bank assays and to sequential chemical synthesis procedures involving the synthesis of compounds through the separation of intermediates prior to the next reaction step. They are applicable to the purification of cells, particles and molecules from complex mixtures.

Importantly, the invention eliminates the need for centrifugation and allows immunoassays to be performed without extraneous wash steps and decanting or rinsing steps. This simplifies the design and function assay instrumentation and automation, as well as the containment of hazardous materials in the reaction vessel.

As noted in this Specification, this Application is a Continuation of U.S. Ser. No. 11/715,411 filed Mar. 8, 2007 which is a Continuation-in-Part of U.S. Ser. No. 11/518,189 filed Sep. 11, 2006 which claims the benefit of U.S. Provisional Application 60/716,591 filed Sep. 13, 2005, said U.S. application Ser. Nos. 11/518,189 and 11/715,411 being incorporated herein by reference for all purposes as though repeated herein verbatim in their entirety, claims and abstract included.

In the preferred embodiment, materials of interest that are to be assayed, purified or processed are rendered magnetic by the attachment thereto of a magnetic particle tagged binding partner of the material of interest the preferred moving force is a magnetic field and the zones are layered on the basis of density and non-miscibility. More particularly, magnetized target reactants are moved by a moving magnetic field from the fraction of the reaction mixture into a layered zone of specific gravity greater than any of the reactants and specific gravity of the solute mixture. Materials of lower specific gravity are excluded from entering the dense layer by the phenomenon of flotation; they simply float on the surface of the dense layer according to Archimedes' principle unless purposefully forced under by applying the appropriate force, thus becoming separated from materials of interest that have been moved under by the magnetic force. Because flotation is absolute, this results in ultra clean separation, which is often very desirable in many procedures.

As can be seen from the above, this invention is directly applicable to any immunoassay where it is necessary or desirable to provide one or more separation steps during the assay, such as in separating bound and unbound materials from a complex prior to the detection step. For example, in a sandwich assay such as for HBsAg or B-hCG, an antibody to first determinant ($Ab_1$) on the antigen is tagged with magnetic particles and a second labeled antibody to a second determinant ($Ab_2$) is mixed with the sample. Following incubation, a complex of the Mag.antibody.antigen.second antibody with label is formed. The labeled antibody attached to the complex is separated from any unbound labeled antibody by the application of a magnetic field which moves of the magnetic particle complex through a more dense layer to a detection zone while the unbound labeled antibody floats to the top of the zone.

The method also applies to the ToRCH Assays, i.e., Toxoplasmosis, Rubella, CMV and HSV. In this case, the disease related antigen (i.e. Rubella hemaglutinin antigen) is bound to the magnet, any antibody to Rubella antigen in the patient's sample reacts with the antigen on the magnet and then is separated from the unbound IgG in the sample by moving the complexed particles through a separating zone and into contact with a labeled antiglobulin reagent which reacts with patient's rubella antibody if present.

Examples of the invention in several applications

Some examples with varying combinations of previously described requirements will now be given before exploring more detailed aspects and issues of the invention: These methods include utilizing:

1—two continuous liquid zones, the first zone being or comprising the sample liquid and particulate reactants and the second zone being a liquid zone with greater specific gravity than the reactants.
2—binding partner coated with magnetic particles wherein the binding partner is a capture antibody to MOI, or a lectin that can react with tagged red blood cells (Example 1), or magnetic particles coated with an antigen from an infectious agent such as HIV or Hepatitis C (Example 2).
3—magnetic field to move particles.
4—buoyant force to move particles.
5—a capture surface zone coated with an antibody (anti Human IgG in the examples) reactive with the material of interest in the complex (human IgG in the Examples).

EXAMPLE 1

Blood bank indirect antiglobulin test for crossmatch, antibody detection or indirect typing With a human typing reagent substituted for patient serum. A microtiter plate with the bottom of the wells coated with mouse anti-human IgG antibody is provided. A separating zone is placed on the bottom of the wells. A suspension donor or reagent of red cells and patient serum and magnetic particles coated with a universal red cell binding reagent such as a lectin or mouse anti-human red blood cell antibody. (Note: to simplify pipetting addition steps and increase the serum-red cell ratio, the red cell suspension may be pre-tagged with the magnetic particle). After appropriate mixing and incubation, the magnetic particle complex is moved through the separating zone by a magnetic field and on to the anti-human IgG antibody coated onto the well surface. The magnetic force holding the complex against the bottom of the well is released and the cells not bound by the anti human IgG reagent allowed to float or be agitated off of the bottom. The visible attached red cells indicate a positive crossmatch.

EXAMPLE 2

Test for Antibody to HIV or to Hepatitis C virus (HCV) or to cytomegalo virus (CMV).

The bottom of the well is coated of a microtiter plate with mouse anti human IgG antibody and overlayed with a separating zone. Patient serum is added and magnetic particles coated with an antigen from the infectious agent of interest is added. After appropriate mixing and incubation, the magnetic particle-antigen-human antibody (if any) complex is forced through the separating zone and on to the anti human IgG antibody coated surface. After reaction (if any) with the IgG antibody, the magnetic force holding the complex against the bottom of the well is removed to allow complex not bound by the anti human IgG reagent to float or be agitated off of the bottom. Measure any attached particles.

EXAMPLE 3

Sandwich Test for Antigen. The bottom of a microtiter well is coated with one antibody to a determinant on the antigen and the magnetic particle is coated with another antibody to the antigenic determinants. The specific gravity of the magnetic particle (for example 1.1 to 1.3), the suspending liquid (for example 1.0 to 1.15) and the sample (for example 1.0 to 1.15) are less than the specific gravity of the dense separating liquid (for example 1.3 to 2.0). The magnetic particles themselves can be used as both a reactant and a label. All reactants and separating liquid can be in the vessel prior to the addition of the sample and because of the orientation of the vessel and the specific gravity of the liquids and magnetic particles maintain the order from top to bottom, magnetic particles, separating liquid, antibody coated vessel bottom when the less dense sample is added and mixed with the magnetic particle suspension in the top sample and magnetic particle zone. Following incubation the magnetic particles complexed with the antigen (MOI) if present, or not complexed with the antigen if absent, are moved by application of a magnetic force through the dense separating liquid and to contact with the antibody coated vessel bottom. The magnetic particle-MOI-antibody complex will form if the MOI is present in the sample. The magnetic force is removed and unbound magnetic particles will float off the bottom surface because the particles are less dense, more buoyant, than the separating liquid. Observe the bottom reaction surface for the presence of bound magnetic particles and detect those bound particles.

EXAMPLE 4

Pregnancy test—This example can use the standard separating zone in addition to the sample zone or utilize only one separating zone, the urine sample itself. The magnetic particles are used as the label in this test. The test vessel contains a reactive surface coated with a first antibody to hCG, and a magnetic particle of low specific gravity coated with a second antibody to hCG. Add the sample to the vessel, mixing the less dense magnetic particles with the sample, apply a magnetic field to force the magnetic particle hCG complex through the separating zone (urine sample) onto the reactive surface. Remove the magnetic force holding the complex against the bottom of the vessel and allow the unbound complex to float, agitated or decanted off the reaction zone. Measure or observe the attached particles.

EXAMPLE 5

Pregnancy test with a direct label.—A vessel, or a microtiter plate array of wells, with a dense separating zone in place at the bottom. Add first a labeled antibody specific for the analyte, then a second antibody [specific for the analyte] attached to magnetic particles. Then add patient urine sample. After appropriate mixing and incubation, apply a magnetic field to force the magnetic particle complex through the separating zone to the bottom of the well. Measure the attached label.

EXAMPLE

Pregnancy test With indirect label. A vessel, or a microtiter plate array of wells, with a dense separating zone in place at the bottom containing a substrate for an enzyme, and an intermediate separating zone above the substrate zone is provided. Add a first antibody labeled with an enzyme and a second antibody attached to magnetic particles and patient sample. After appropriate mixing and incubation, force the magnetic particle complex through the separating zone and into the substrate zone. After waiting the appropriate time measure the substrate that has been converted to product by the enzyme label. Measure the product developed.

EXAMPLE 7

Direct Blood typing—In a vessel or micro titer plate with a denser separating liquid zone such as a fluorochemical or an isotonic Ficoll® solution in place on the bottom of the wells, add a saline suspension of red blood cells and a magnetic particles coated with specific red cell antibody, for example anti A, to an antigen that may be present on the red cells. After appropriate mixing and incubation force the magnetic particle complex through the separating zone and measure any attached red cells, obtaining the signal by absorbance measurement of hemoglobin or the hemoglobin signal enhanced with benzidine.

EXAMPLE 8

Blood blank or cell antigen detection using a sequential approach. In a microtiter plate with a separating zone on the bottom and a labeled antibody zone above that and another separating zone above the labeled antibody zone add cells and a capture antibody specific for a cell type bound to a magnetic particle. After appropriate mixing, force the complex through the top separating zone and into the labeled antibody zone and ultimately through that zone and through the bottom separating zone. Measure any attached label in the complex at the bottom of the well.

EXAMPLE 9

Synthetic Processes of either research or commercial scale. For some processes or systems it may be desirable to have one single separating zone beneath multiple reactant containing zones that are separated from each other by baffles extending into the separating zone. For example, consider a bottomless microtiter plate partially immersed in a tray containing a liquid separating zone such that the separating zone creates the "bottom" of each microtiter baffled zone. Place various reactants in each of the microtiter wells and move reactants from one well to another well through the separating zone. This description is not intended to limit this description to small volume baffled containers as described but also applied to very large baffled systems with a common separating zone or zones.

EXAMPLE 10

A Typical Competitive Binding Assay A sample of serum which contains digoxin, is treated simultaneously with digoxin antibody tagged with magnetic particles and digoxin reagent binding partner of the antibody of the Mag.antibody reagent, said binding partner being labeled with an enzyme. A competitive reaction occurs with the sample digoxin and the labeled digoxin competing for combination with the Mag.Ab reagent. The reaction products, Mag.Ab.Ab and Mag.Ab.Ag. are formed. After the reaction, the magnetic particles are subjected to a magnetic field force to pull them through a liquid medium denser than the unreacted components. As they travel, enzyme labeled digoxin particles not bound to containing the magnetic tag will either stay in solution or float to the top of the dense layer and the enzyme label bound to the magnetic particles is moved to a substrate zone. The determination of the presence and quantity of digoxin is then measured by evaluation of the reacted labeled digoxin reagent in accordance with known, competitive binding protocols.

Introduction of samples. In general, samples to be studied or processed will be introduced onto the top layer where they may react for a time before the next step moving certain reactants selectively down into and through more dense layers. Thus, it may be important that this top sample introduction layer be of lower specific gravity than the next layer below. In this regard, since some magnetic particles have a high specific gravity, it may be necessary in the case of some reagents to coat particles to adjust their buoyancy to make sure they remain suspended in the top layer until forced down. Those skilled in the art are aware of the procedure for doing this. Even if the particles are of a density that would sink without mixing they can be mixed in the sample-containing solution, by proper selection of the separating solution so that it is more dense than and immiscible with the sample containing solution. The amount of contact time between the capture particles and the sample can also be controlled by adjusting volumes, viscosity, time of addition and other parameters.

Enhancing and speeding reactions by mixing. Oscillating magnetic fields or ultrasound pulses focused on a particular zone to cause particles to move with rapid movements or oscillating motions over a short distance. Such movement or oscillations may be used when reactions are going on to enhance and speed reactions in particular zones and may also be used to free materials not of interest from contaminants that are absorbed onto but not bound to the mag-particles, so they are released and become free to float back up into less dense layers above. It is also possible to apply mechanical mixing forces, such as the use of rotator platforms, to cause gentle mixing within zones but not between zones.

Zones. Design and selection of the separate zones in the continuous liquid medium may be selected based on the specific gravity of the reactants, sample medium, and reaction product of the test to the invention. The multiple zones of the liquid medium may differ from each other in various ways, such as their density or miscibility or surface tension or hydrophobicity or hydrophyllicity, and are designed for each laboratory procedure or industrial process so that certain entities can be selectively forced to enter and or pass through a particular zone which other materials will not or cannot enter, either on the basis of their natural properties, such as density, or on the basis of a property acquired from a particular treatment.

Zones may be chemically inert and designed simply based on their physical properties such as for example specific gravity and interfacial tension to exclude particular materials. In certain cases, the zones may contain reagents or other substances that react with materials of interest and transform them in an intended fashion as they pass through a particular zone of the continuous liquid medium. The separating solutions can range from the extremely inert and dense fluorochemicals, oils, and organic solvents, to aqueous solutions of various pH with or without additional reactants contained in them. To aid those skilled in the art in selection of separating zones, consideration should be given to the known or measured specific gravities of known materials all in consideration of the densities of the materials involved in the test. For example, acetone and benzene have a density below 0.9, many solutions of materials dissolved in water can be adjusted to densities from 1.0 upward depending on the solubility of the solute in water, and many organic molecules and fluorchemicals have a density greater than 1.5. Aqueous solutions of urea or guanidine, used for the dissociation of molecular complexes, generally have a specific gravity between 1.1 and 1.17. Other important values are: Urine, about 1.03 or less, serum, about 1.06, red cells, about 1.09-1.15 Dynal magnetic particles, about 1.3, fluorochemicals vary from around 1.5-2.0, including perfluorooctyl bromide, perflurohexane, various Fluorinert® 3M Materials. A RBC-mag particle complex, being less dense than the separating layer will usually range from about 1.1 to about 1.2 using Dynal particles of about 3 micron average particle size. The following chemicals have the specific gravities noted for them:

| CHEMICAL | SPECIFIC GRAVITY | REFERENCE |
|---|---|---|
| Perfluorohexane | 1.682 | F2 Chemicals Ltd.* |
| Perfluoro-n-octane | 1.75 | F2 Chemicals Ltd. |
| Perfluorodecalin | 1.917 | F2 Chemicals Ltd. |
| Perfluoromethyldecalin | 1.972 | F2 Chemicals Ltd. |
| Perfluoroperhydrophenanthrene | 2.03 | F2 Chemicals Ltd |
| FC-40 | 1.85 | 3M Company** |
| Perfluorotributylamine (FC-43) | 1.9 | 3M Company |
| FC-70 | 1.94 | 3M Company |
| FC-73 | 1.68 | 3M Company |
| FC-77 | 1.78 | 3M Company |
| 1,2 Dichloroethylene | 1.27 | |

*London England
**Minneapolis, Minnesota

Isotonic Ficoll® 400 solutions cover a density range up to 1.2 gm/ml and amino acids, sugars and proteins can be used to make aqueous solutions of various specific gravities.

The density of various molecules and their solubility characteristics are readily available in reference manuals such as the CRC Press Handbook of Chemistry and Physics (Chemical Rubber Co.).

Especially suitable in the invention are hydrophobic fluorochemical layers, in between or adjacent to hydrophilic aqueous layers or surfaces, with the specific gravity of each carefully chosen to increase or decrease in the correct order, depending on the test. They should also not irreversibly mix if shaken up by violent movement during shipping and should settle back to separate and correctly layered materials upon removal of the movement.

The materials should be inert to the components of the test, so as not to react with or alter cells or other mag-tagged materials as they pass through. Fluorochemical liquids of relatively high specific gravity are useful in creating a significant buoyant force to remove unbound materials from a surface. Other layers, for example organic solvents may be selected for a desired reactivity. They can be very thin. One purpose is to improve separation of aqueous layers or surfaces.

Other methods used by the invention to maintain separation of layers are the use of solid state baffles, meshes within the layers both with interstices or pores large enough to freely allow migration of magnetic particle complexes but which would prevent convective or other current flows that might cause intermixing of layers. Physical material, fixed or free, separating or retarding the mixing of adjacent layers such as filters, baffles, or constrictions of the vessel can assist in maintaining the zone stability.

Other methods involve treating the vessel, particularly the walls or select wall sections to make use of surface tension effects relative to the vessel wall and the liquid zones to prevent or control intermingling of layers.

As a statement of general applicability, in selecting the various densities for the assay construct of the present invention, the specific gravity of the uppermost layer just below the zone of sample addition should be equal to or greater than the specific gravity of the sample, typically serum or urine or cell suspension, and the specific gravity of the soluble materials in the sample mixture. The top zone of sample introduction may contain reagents including mag-tagged reagents. Once the sample, first zone reactants and magnetic particles are mixed, the specific gravity of the soluble materials may decrease slightly, as soluble sample materials such as proteins are further diluted in the solute for the magnetic particle reagent and other reagents or diluents, helping to keep the layer with the sample in place on top of the adjacent zone.

When the zones are oriented in a top to bottom configuration, subsequent lower zones have a specific gravity higher than the next higher zone. Some zones may contain reaction products which will add to or modify the complex. Subsequent zones will purify complexes from non-reacted materials as the complex moves through the zones.

The invention envisages a whole new series of novel liquids employed in novel layers to obtain the necessary properties to exclude entry of unwanted materials including non-miscibility, specific gravity, chemical reactivity or inertness. Specialized zones, which may contain reactants, will be required by the various novel methods, procedures and processes now made possible by the invention.

Forces—In the invention various forms of force may be used to move materials of interest differentially through the zones of the continuous liquid medium, and onto surface capture zones. The preferred force of the invention is application of a magnetic field to move the magnetic particles, changing direction of or removing the magnetic field as necessary, to separate magnetized reactants from non-magnetized entities and in or through layered zones appropriate to the test specific gravity and the intensity, direction and timing of the magnetic fields may changed as suited to the steps of the procedure. Other forces used selectively or combined in the invention include, for example, sedimentation, under gravity or by centrifugation, flotation, electrostatic charges, electrophoresis coordinated with selected properties of the liquid zones such as density or hydrophilicity to admit passage of materials of interest and exclude MNOI.

The invention also envisages using mechanical forces physically moving reactive surfaces that have material bound to them down through dense layers so as to float off unbound materials and purify the bound reactants. And moving dense liquid layers up past fixed reactive surfaces where reactants are bound to remove unbound reactants by shear or buoyant force.

Novel Reagents—Many research and commercial reagents are presently available containing antibodies or other ligands with magnetic particles attached. These reagents are able to attach magnetic particles to materials of interest and are useful in methods where a magnet is used to pull the complex to the vessel wall to separate it from other materials. Then materials not of interest are, aspirated, decanted or otherwise removed, and the remaining materials of interest can be resuspended and studied in isolation.

Dynabeads come with a variety of immunoreactants bound to them and come in various diameters and specific gravity. For example, some Dynabeads are 2.8 microns in diameter with a specific gravity of 1.3 grams/cubic centimeter.

Readable indicator labels such as enzymes, fluorophors, chemiluminescent materials, radioactive isotopes, and other labels may be attached to materials of interest in addition to magnetic particles and they may be read when delivered to a final reading zone on the magnetic complexes. These novel reagents apply to many assays, diagnostic tests, separative procedures and chemical syntheses.

Other novel reagents contemplated by the invention are mag-cell reagents, for example, reagent red blood cells of known blood type complexed with magnetic particles, to be used for blood bank diagnostic tests.

Another reagent is a liquid dense enough to sink to the bottom of the vessel, for example, a fluorochemical, below the other zones which is added at test reading time to float off MNOI not specifically bound to the bottom surface antibody.

The invention also contemplates having reagents coated on a surface, for example at the bottom of the vessel, which can react with and capture complexes forced against it.

Zones for Delivery of Materials of Interest . There is usually a need to measure the quantity of the isolated purified material that was present in the original mixture sample. But often it may need to be collected and removed for further operations upon it. Thus, the invention envisages various types of harvest zones to which highly selected materials of interest from a starting mixture can be delivered, where they may be harvested and subjected to further downstream processing.

In one embodiment of the invention the bottom surface of the well is transparent so that materials delivered to this surface can be examined microscopically in situ. And the bottom surface of the vessel can be a removable; in the form of a glass slide for staining for microscopy. Or, when live cells are delivered for tissue culture, the bottom surface may be a removable culture (Petri) dish.

In all, delivered cells may be studied by many varied downstream procedures including, for example, immunohistochemistry, confocal microscopy, PCR for molecular studies or RNA expression profiles.

When implementing ELISA immunoassays in the invention, chromogenic or fluorogenc substrates sited in the delivery zone may await the delivery of enzyme linked analyte complexes to provide a signal that can be measured.

Therefore, in assays, signal acquisition may be achieved by instrument systems normally used in the art, in addition to visual observation of accumulated cells in appropriate tests or scanning the test construct or viewing the construct with a CCD video camera with appropriate pixel processing software. Instruments such as a fluorescence microscope or reflection densitometer may measure specific signals from labeled analyte complexes.

In one embodiment, mag-antibody tagged materials of interest are delivered by magnetic field force through a liquid layer denser than the complexes themselves to a surface coated with antibody specific for the analyte. There they attach by the sandwich principle. Some of these delivery destination areas may have specific capture mechanisms, such as surface attached antibodies or other ligands. to hold the material there after the magnetic field is removed.

Other embodiments of capture make use of study of material release after the magnetic field is removed to obtain information. When the magnetic field is turned off all materials not immunochemically bound by the surface antibody will detach from the surface and float up into the dense liquid layer, if it is denser than the complexes themselves. This freeing may be enhanced by agitation or swirling. One improvement to this scheme is to print the antibody on the surface in a recognizable two dimensional pattern such as a cross or circle or alphanumeric character. Such a pattern will both represent a positive test result and act as its own control, minimizing signal noise and eliminating false positives due to non-specific contaminants.

Reading, signal processing. When the magnetic particles are coated with typing antibodies or red cell capture antiglobulin reagent, the simplest and easiest way to measure the presence and quantity of red cells bound to the magnetic reagents either in flow or stopped on a magnet is a densitometer scan reading through a hemoglobin wavelength filter. An alternative is a CCD color camera with pixel assessing software. In certain situations, chemical amplification of the hemoglobin signal using a chromagen. e.g. tetramethyl benzidine (TMB) chromagen/substrate solution would be worthwhile. Enzyme amplification is another method of use. Often, visual observation is suitable for qualitative determination Harvest Zone. The invention envisages, in some embodiments delivery of MOI to a harvest area where highly purified proteins and other materials may be collected for further use, including for commercial manufacturing.

In the case of separated cells, which can be delivered live and fully functional in the invention, studies of highly selected living cells can be done with confocal microscopy, laser scanning, FISH and other sophisticated procedures. Also, delivery of cells to microscopic slides to other surfaces for counting, staining and microscopic examination, delivery to cell media for cell culture, or for molecular studies such as PCR.

Various indicator labels such as enzymes and their substrates, reporter molecules like fluorophors, chemiluminescent materials, radioactive isotopes, and other labels may be attached to the appropriate reagents, especially to non-magnetic tagged anti-human globulin, and analyte proteins in the manner well-known in the immunoassay art and thus serve to act as the element by which the progress and results of the test may be observed and measured during the test run. In assays that utilize red blood cells, the hemoglobin in the cell can be used as the label for reading. In cases where a complex can react with a terminal surface, for example be immunochemically bound to the surface, the magnetic particle could be used as a label. The magnetic reagents can be prepared by methods well-known in the art. Magnetic particles attached to proteins have been made in the art and are well-known. Their process of preparation is well-known. When such labels are used in the method of the invention as a means to visualize the end point, suitable substrates or exciting media should be supplied at appropriate places in the assay construct.

Capture and Release Testing. The invention contemplates creating surface capture zones, by printing specific reagent antibodies on selected areas of the inside surface of the vessel. Inside surface areas coated with reagent antibody would selectively capture and bind MOI complexes forced there but not MNOI that might accompany them. Such inside surface areas although not liquid zones, may be considered zones that MOI can enter and be captured on and MNOI excluded or repelled from by various methods.

In one embodiment of the invention, a transparent bottom surface of the vessel becomes both a capture and test reading zone. It is coated with an antibody reactive with the MOI complex so that any magparticle-MOI complex forced by a magnetic field onto this bottom surface will be captured and held there by the surface bound antibody.

The invention contemplates then removing the magnetic field and applying a measured degree of a counter force able to eject complexes off the surface. The degree of this force will be calibrated to remove non specific adhering MNOI but not break the antibody bond to MOI which will stay attached to be read. The purpose is to eliminate false positive tests due to signals from unwanted non specific MNOI that may persist on the surface.

The preferred counter force of the invention is flotation force. This is created by adding or having present a resident bottom liquid layer denser than the MOI complexes and any MNOI contaminants. The purpose of this dense layer is to create a relative buoyancy counterforce that will provide flotation and float off any material not specifically bound to the surface by surface antibody. Then the signal from the labeled MOI complex persisting on the transparent surface is read from outside the vessel.

Controlled gentle consistent release may be obtained by introduction of a dense layer into the vessel at read time, which will sink to the bottom and float off any material not actively bound to the floor, leaving the bound material to provide a clean signal. The benefit of adding this heavy liquid layer to the vessel after the MOI has been captured is that it may be made much denser than would be desirable in a resident bottom flotation layer that the mag-complexes would have to be forced through to the capture surface by a magnetic field. The addition of a liquid of greater specific gravity than the MOI complex at the end of the process allows for the use of centrifugal or gravitational force to create contact with a reactive surface and still utilize buoyant force to remove the unbound complex.

Another type of counter force contemplated by the invention to be applied to test for specific binding of MOI after the magnetic field is removed is, for example, electrostatic force. This can be created by coating the surface with a negatively charged molecule such as heparin alongside the capture antibody which will repel negatively charged proteins, and cells since all cells carry a negative charge on their surface. The invention includes modulating the charge of amphoteric materials with buffers that adjust the pH of this zone so as to increase the charge on molecules and so increase the electrostatic repulsion force.

A third counter force that the invention may use is to reverse the magnetic field, to test for specific binding of mag-MOI complexes by surface antibody. The reverse magnetic field force would be calibrated so as not to break the antibody bond holding MOI but still force off any non antibody bound magnetic complexes that are present.

The invention contemplates any other suitable counter force to the antibody binding that may be applied to differentiate bound from non bound materials at the surface.

Other embodiments of capture-release reading make use of the timing and rate of material release after the magnetic field is removed.

Although many current tests make use of surface bound antibody capture, none combines this with magnetic fields and a coordinated repelling buoyant counter force to create exquisite test specificity and sensitivity.

Methods for release of magnetic particles from materials of interest. Some of these procedures, especially purification processes, require release of magnetic particles before more processing is performed. Release of magnetic particles from materials they are bound to can be achieved in various ways by those skilled in the art before processing steps are continued. This dissociation of material of interest from the particles is particularly valuable as a step in the purification of cells or molecules and can involve urea or guanidine solutions, pH changes, enzymatic cleavage and other means.

Instrument and System Formats
Generic Schematic of a Device

Reference is made to the schematic representation appearing below showing a generic version of a device useful in the invention. It represents liquid layers of different densities in a liquid column contained in a vessel (not shown) such as a microtiter plate well. In the device, n, m and p are zero or an integer designating that such zones may or may not be present. The device comprises preferably a plurality, i.e. at least two layers of different density, one of which may be the liquid sample. For some tests, only one layer need be present, In addition, there may be more zones than those indicated, and overlapping of zones depending on the specific immunoassay being performed and the desired location of reagents. The bottom surface of the vessel in contact with the liquid column is also considered a zone. Each zone is contiguous with the adjacent zone and the device terminates in a magnet which can be activated or deactivated at will. It may also be moved to various areas of the device.

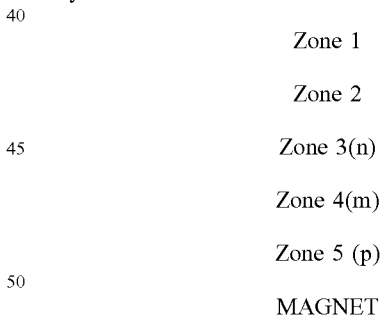

Zone 1

Zone 2

Zone 3(n)

Zone 4(m)

Zone 5 (p)

MAGNET

The materials of Zone 1 and those following have specific gravities dictated by the sequence of the steps of the particular assay, the reagents and sample. In general, proceeding from the uppermost to the lowermost layers, they will increase in specific gravity and otherwise be so designed that the lower specific gravities of unbound reactants in the assay system remain in the lower density layers while the reacted reagents settle or are forced into the higher density layers and ultimately against the vessel wall at the bottom of the liquid column. The separation of these zones of different density can be enhanced by selecting materials that are poorly miscible with each other e.g., oil, fluorochemical liquids, or oil-like materials and water wherein the oil may be of higher or lower density than the water. The vessel wall, typically at the bottom of the liquid column, can contain reactive material such as an immobilized antibody or antigen. The concept of the invention is aided by the use of the magnet which attracts the reacted magnetic complex yielding a much faster settling of the reacted tagged reagents to the magnet area than would occur by simple gravity and elapsed time. The specific gravity of the complex containing the MOI can be less dense than the liquid zone above the vessel wall reactive zone, thus allowing the use of buoyant force to remove unbound material from the surface by floatation.

Role for the Invention in Automated IVD Instruments

The preferred embodiment of the invention for use in an automated testing instrument is to make use of microtiter plates and the automated liquid handling and robotic systems that are widely available to serve them. Microtiter plates and pipetting, mixing and reading systems are common laboratory tools. When Dynal Mag particles (around 2.8 microns) are used in microtiter plates, immunoassays or blood bank procedures, $0.1 \times 10^6$ to $1.0 \times 10^7$ Mag particles per well are sufficient.

It is possible to perform a large number of diagnostic tests such as sandwich immunoassays or indirect anti-globulin blood bank tests. Following the procedures as described for single vessels, the automated instrument of the invention employs kits comprising microplates with wells prefilled with mag-particles and labeled reagent antibody, a denser liquid separation layer, and capture antibody printed on the bottom surface as described. To perform tests, unknown samples are pipetted into wells by the robot systems, a magnetic field applied and released, and the captured MOI label read from below.

Because of the large number and great variety of combinations and permutations of reactants and reaction schemes possible, the device is presented in connection with particular reference to the procedural aspects of the device. Those skilled in the art will easily be able to adapt the construct to a specific assay and configuration.

Array of Bottomless Vessels Format

One instrument format for use in chemical synthesis processer of the invention, is an array of bottomless vessels placed into a bath containing a layer of an inert dense liquid, for example a fluorochemical, such that there is a continuous liquid connection between all the vessels through the fluorochemical layer in the bath. The upper surface of the fluorochemical layer is now the functional bottom of each well for all suspended materials except mag-complexes that can be forced into the bottom layer by magnetic field force. By applying a magnetic field, magnetic reactant complexes are forced down into this layer leaving behind any other unwanted reactants in the liquids of the vessel. Highly purified complexes are then moved laterally by relocating the magnetic force, then allowed to float up into an adjacent bottomless vessel where the reactants for the next stage of the process await them. In this manner, a long series of chemical synthesis steps can be performed on the magnetic particle complex with absolutely no carry over of reactants from previous steps. The advantage of this instrument format is there are no moving parts, no volumes of washing solutions and no liquid handling pumps and no toxic waste sinks.

Examples of Applications

IVD Tests
Immunoassay Applications

General Method for Immunoassays: Provide a first reactant or binding partner, typically an antibody to an analyte to be detected (such as hCG or HBsAg), attached to a movable surface, for example a magnetic particle if magnetic forces will be used, or a plastic surface, such as a flat surface if manual movement of the object is to be used.

1—Mix the first reactant for an appropriate time with a sample suspected of containing the analyte that can react with the first reactant and a labeled reagent capable of reacting with the reacted analyte or competing with the reacted analyte for combination with the first reactant.

2—Separate the first reactant from the unbound label by applying a force that will move the complex through a solution that will create a separate cleaning zone. This solution ideally will stay separate from the original mixture and could be more dense or less dense than the original mixture and may be immiscible with that mixture such as oil and water.

3—Move the complex to a reading zone which can directly detect the label or where the label can further react with a substrate to create a material that will be detected in the reading zone.

In some immunoassays especially to assay for a state of immunity (for example immunity to Rubella) which involve a labeled antiglobulin reagent it is desirable to separate the sample and first reactant complex from unreacted sample prior to exposing the complex to a labeled antiglobulin reagent. This is accomplished by adding a 1st separation step prior to the addition of the labeled antiglobulin reagent.

In fact, the second variation described above can be further simplified for a home pregnancy test by utilizing a very low specific gravity magnetic particle (for example less than 1.0) in conjunction with the urine sample (1.0 to 1.03). This simplification will bring the magnetic particles through the urine sample and into contact with the reactive surface by applying a magnetic force, and removing the unbound particles because of their buoyancy and by agitation, such as discarding the urine from the container after the magnetic force is removed. The reaction zone is observed for bound magnetic particles.

Immunoassay Antibody Detection Method

The method also applies to the detection of antibody to disease related antigen in a sample such as the ToRCH assays—Toxoplasma, Rubella, CMV, HSV—which are often performed in a sub-population of women of child-bearing age and infectious diseases assays of interest in blood banking such as Hepatitis C (HCV), HIV and CMV which are used to exclude blood for transfusion. In these assays, the disease related antigen is bound to the magnetic particles (for example 0.3 micron and specific gravity 1.3). An antibody reactive with human immunoglobulins is bound to the reactive surface at the bottom of the vessel (microtiter plate well) and overlayed with a dense separating zone (specific gravity greater than the magnetic particles, their suspending solution and the sample). Patient's sample (typically serum, specific gravity less than 1.1) is added to the vessel, mixing with the magnetic particles, and antibody if present in the sample reacts with the antigen on the magnetic particles. The magnetic particle sample mixture is separated from the reactive surface at the vessel bottom by the separating zone until a magnetic force is applied moving only the magnetic particles and any bound immunoglobulin through the separating zone and into contact with the antiglobulin reagent bound to the bottom surface, all unbound sample material remains floating in the first sample zone. After the magnetic particles are brought into contact with the antiglobulin reactive surface the magnetic force is removed and the unbound magnetic particles float off the surface, leaving only magnetic particles with bound antibody (MOI) bound to the surface. The reaction surface is observed for the presence of bound magnetic particles which indicate the presence of antibody to the disease agent in the patient's sample.

Blood Banking

One area in which the invention is particularly suited, is the field of immunohematology, i.e., the set of blood bank laboratory tests that are necessary before blood transfusions can be prepared and administered safely to patients. Briefly, all blood bank serological tests are based upon detecting whether a red cell antibody binds to antigens on red cells of patients or blood donors. The novel magnetic particle methods of the invention can be applied to all of the standard tests of the blood bank laboratory, including immunoassays routinely performed for transfusion transmitted diseases such as HIV and Hepatitis. The invention offers significant advantages in the performance of various esoteric and research immunohematological tests.

The invention contemplates three general test methods in blood banking. Other variants of these protocols are not excluded.

First method: Direct Red Cell Phenotyping

This method employs reagents consisting of magnetic particles directly tagged with specific known antibodies. These reagents are incubated with and attach to red cells that carry the cognate antigen on their surface but do not attach to red cells that lack the antigen.

As described in Example 6 above, magnetic particles tagged with a specific antibody (for example Anti-A) are mixed with red cells which may or may not contain the A antigen. The magnetic particle tagged antibody complexes with the A antigen on group A red cells and will pull those red cells under the influence of a magnetic field to the magnet through more dense liquids. Group O or group B red cells which both lack A antigen will not move under that influence.

Thus, unknown red blood cell antigens may be determined by selecting specific reagent antibodies such as Anti-A, Anti-B, Anti-D and the like, in place of the serum used in crossmatch test above. Similarly, unknown antibodies in serum can be determined using specific reagent red blood cells in the method. Other specific determinations can be made as well be seen below.

The test is read as positive if red cells are observed on the bottom surface of the vessel next to the magnet. In a negative test no red cells are observed on the bottom surface.

The advantage of this method over previous magnetic cell separation methods of having a dense zone is that in a negative test the cells are well separated from the reading zone. In previous methods they are closely adjacent. Thus, a negative test is more clearly differentiated from a positive test. Moreover, no decanting is necessary.

Second Method: Capture and Release by Surface Bound AHG

In this method, red cells of known or unknown blood group, tagged with magnetic particles as described above, are incubated with unknown or known red cell antibodies, respectively.

The magnetic particle tagged red blood cells are pre-prepared and dispensed into the reaction vessel by a single pipetting step. The magnet tagged red cells are then reacted with a reagent or patient sample that may or may not have antibody to the red cell antigens. After sufficient time for the reaction to occur, the magnet tagged cells are moved by the application of a magnetic field through a dense separating solution and to a reactive surface coated with a bound antiglobulin reagent. The magnetic field is removed and bound red cells stay attached to the reactive surface. Unbound red cells float off the surface and into the more dense separating liquid. In a positive test, red cells are observed remaining bound to the capture surface. In a negative test, no red cells are observed remaining on the capture surface.

More specifically, a mixture of donor's red blood cells, patient serum and magnetic particle with a red cell binding partner attached to it (lectin, anti-human red blood cell antibody, or red cell binding chemicals) is prepared and either preincubated or allowed to incubate in the liquid medium.

During the incubation:
1. The magnetic lectin complex will react with any red blood cells since the lectin chosen is a universal red blood cell reactant.
2. Any antibody present will react with just those red blood cells carrying the specific red blood cell antigens, resulting in red blood cells coated with antibody. If some red blood cells become coated with antibody, the AHG test is positive. In no red blood cells become so coated, the test is negative.
3. A magnetic field is applied to the reacted mixture pulling all magnet tagged red blood cells, coated or non-coated, through a dense liquid zone (selected to have a specific gravity greater than the magnetic particles red cell complex) where they are washed free of all proteins except those specifically bound to red cell surface antigens, and on to a reaction zone with immobilized antiglobulin reagent.
4. After the red cell magnetic particle complex has been contacted to the antiglobulin reagent surface the magnetic field is removed and unbound red cell complex (specific gravity typically less than 1.2) is removed from the surface by floatation in the separating liquid of higher specific gravity. The unbound cell complex is less dense than the separating liquid and floats off the surface. The reaction surface is observed for bound red cell complex, indicating the presence of an antibody attached to the red cells.

Third Method: Passage Through Labeled AHG Zone

In this method red cells are tagged with mag-particles and incubated with antibody exactly as in the second method just above. Coated red cells are washed in the same manner. However, detection of the antibody coat is done by moving the cells through a denser liquid zone containing free labeled AHG where coated cells pick up label and non-coated red cells do not. In a positive, test label is observed in the end reading zone. In a negative test, no label is observed in the end reading zone.

Separation of unreacted AHG from the magnetic complex is achieved by drawing the complex through liquid zones of increasing density, so that lighter unreacted labeled AHG will remain in its original lower density regions and will not take part in the reading determination. The effect of the magnetic pull-through is enhanced by providing layers of increasing density gradient as the flow goes through the various zones. By this means, debris and unreacted material will remain in areas appropriate to their densities whereas the heavier complexed materials will be drawn through to the layers of higher density. It should be apparent that the foregoing reaction scheme does not depend upon separation of bound magnetic particles from unbound magnetic particles, but rather on the separation of the bound labeled AHG from unbound labeled AHG.

More specifically
1—attaching a magnetic red cell binding partner, such as a lectin or antibody, to a red cell to facilitate the movement of the cell through repugnant denser zones by a magnetic field, can be done simultaneously with the first incubation step of the assay, the interaction of red cells and serum from different sources. Incubate the reactants of the test with the sample, such as RBCs, antibody, and a magnetically tagged universal red blood cells reactant, such as a lectin, i.e., Mag-lectin as described above, in Zone 1. Allow the reaction, if any, to take place.
2—apply the magnetic field to pull the RBC-antibody-lectin-Mag complex through Zone 2, or Zone 3 if present, and be washed therein and then through a Zone of labeled AHG, for example, enzyme labeled AHG, in a higher density Zone 3 or Zone 4. There the AHG portion of the enzyme labeled AHG complex reacts with the antibody portion of the complex. Unreacted AHG stays in its own density zone.
3—separating the magnet tagged red cells—with bound label from the unbound label by moving the red cells through a denser zone which is poorly miscible with the labeled antiglobulin reagent zone.
4—observing the label directly, or indirectly by moving the enzyme linked particles into a substrate containing zone where an amplified signal can be obtained.

Further Discussion

All of the standard and many esoteric and research immunological tests can be performed by the second method. This includes forward and reverse ABO typing, red cell phenotyping , red cell antibody screening and identification, crossmatching including multiple donor crossmatching, detection of minor red cell populations and fetal maternal hemorrhage studies.

ABO forward typing of patients and donors and Rh typing may be performed readily by the first method using mag-tagged anti-A and anti-B reagents. Reverse typing may be performed by the Second or Third method using novel reagents, pre-mag-tagged known A1 and B cells, and patient or donor serum. Antibody screening and antibody identification may be performed by the Second or Third method using novel reagents, mag-tagged known O cells, and patient or donor serum. Antiglobulin crossmatches may be performed by the Second or Third method by tagging donor cells with mag-particles and incubating with patient serum.

One particular example of the First Method is given to illustrate one practical example of use of the invention in a blood bank laboratory test to detect and quantitate fetal red cells in blood samples from Rh-negative mothers. FMH testing is very important in the field of perinatal medicine but present methods are inadequate. This procedure is done for every Rh negative mother who has delivered an Rh positive baby. The magnetic method can be easily adapted to perform this test. In this example of the Direct Mag-Particle Test, magnetic particles coated with anti-D (Rh) react with any Rh positive fetal cells in the Rh negative mother's blood sample and with the application of a magnet separate the fetal cells from the mother's cells. In the preferred embodiment of the FMH procedure, the magnetic particle test kit procedure would be as follows:

A maternal red cell suspension is introduced into a vessel containing a top layer of anti-D magnetic particles solution in a layer less dense than the layer below. Anti D Mag-particles will bind to Rh Positive fetal red cells but not to any Rh Negative maternal red cell. After the red cells react with the magnetic particles, a magnetic force field is applied to pull the Rh positive fetal red cells attached to magnetic particles down the through the denser zone and to the bottom reading zone where these magnetic bound cells can be quantitated. In one preferred embodiment, the magnetic field is applied at the underside of a microplate in which the test solution is added to the mother's red blood cell suspension. The degree of magnetic force applied to the membrane may be selectively adjusted to vary the width or surface area of the capture line or zone.

The fetal cells are quantitated by measuring the density of red cells stopped in the capture reading zone of the column. Read OD in capture zone using a colorimeter.

The key reagent is a suspension of magnetic particles (iron) that are coated with anti-D antibodies. These may be prepared by techniques well-known in the art. The concentration of the magnetic particles and mother's blood used in the assay will be important and needs to be standardized, but in general there should be an excess of magnetic particles to the expected maximum fetal cells in the assay.

Testing Donors for Transfusion Transmitted Diseases.

Tests for antibody in human serum reactive with infectious disease agents such as HIV, HCV, CMV. These methods utilize the same separating solution and antiglobulin coated reaction surface in vessels, such as microtiter plate wells, as the General Blood Bank Assay, but differ in the utilization of an antigen coated magnetic particle in place of a red cell capture magnetic particle. The immunoassay antibody detection method for infectious diseases can be done in parallel with the other blood bank assays utilizing the same general format and timing sequence.

The practical advantage to the blood bank of methods using the invention is that all of the immunohematologial and infectious disease tests required for pretransfusion testing of blood donors can be done in the same microplate, on the same automated instrument at the same time. This would lead to great simplification of logistics of patient and donor specimen handling and aliquoting for the laboratory.

For detection of specific antibodies in patient's serum, such as A-antigens, B-antigens, or O cells and Anti-A, Anti-B, and Anti-AB, the test is run in the same way antibody screening is performed. In either case, the reactants in the form of the magnetically tagged reagent cells or reagent antibodies are added directly onto Zone 1 and allowed to react therein and then pass into other Zones of higher density. Immobilized AHG or labeled anti-human globulin (enzyme label, for example) present in a lower zone is used to either immobilize or label any reacted complex for detection.

Mag Crossmatch

The reaction sequence for a positive crossmatch using a labeled AHG reagent can be described as follows:
1. antigens (–donor red blood cells)+antibodies (recipient serum)+Mag-lectin→Maglectin.antigens.antibodies
2. apply magnetic field to move complex to the AHG.enzyme zone→Mag-lectin antigens.antibodies+AHG-enzyme→a) Mag-lectin.antigens.antibodies.AHG.enzyme (if negative—no reaction here)
b) Mag-lectin.antigen.antibody.AHG.enzyme on magnet move to enzyme substrate zone for color development showing positive. No color indicates negative.

The foregoing is illustrative of a crossmatch blood bank test, but also describes any blood bank serology method by substituting either antisera for patient serum or reagent red blood cells such as screening or reverse grouping cells for the donors in a liquid phase system, The Mag-lectin reagent enables a method for performing all blood serology tests with the labeled or immobilized antiglobulin reagent, and using only regular non-magnetic reagents in addition (for example antisera such as anti-A or anti-D). This eliminates the need to develop a whole series of magnetic reagents of different specificities in the preferred embodiment.

The reading of the labeled AHG is facilitated by providing a suitable substrate for the label at the reading zone of the assay construct. To create the labeled antihuman globulin (AHG) reagent, rabbit anti-human gamma globulin is bound to a detection label such as an enzyme, (e.g. horseradish peroxidase, Beta-galactosidase, etc.) a fluorophor, chemiluminescent material, radioactive isotope or the like, as is well-known to one skilled in the art.

It should be noted that the foregoing reactions apply to the determination of any blood constituent by the appropriate selection of reagents and magnetic and tagged particles.

The present invention enables the separation of bound Mag particles from unbound Mag particles, if desired, through the judicious selection of the specific gravity of the intervening layers.

Microscopy. This principle of removing unreacted cells or debris from those tagged with magnets can also be applied to microscopy. In microscopy, it is desirable to decrease the amount of debris from the viewing field. Since the debris is typically composed of cellular material and fibers or dust, these materials can be removed by flotation by pulling the magnet tagged cells through a solution with a specific gravity that exceeds that of the cells and debris alone, and delivering them to the surface of a microscope slide for staining and microscopic examination in a clean field. The floating debris may be rinsed away before microscopic viewing or it may be rendered invisible by being in a separate depth of field above the separation layer. For example, a thin layer of dense fluorochemical on the slide will prevent debris contacting the slide and allow for the removal of the debris floating on top of the fluorochemical layer while the selected material attached to the magnets is held on the slide.

Cell Separations. The invention, when used for separation of cell types, also provides for novel, magnetic-particle tagged or capture antibody reagents which react with cell surface antigens the blood group antigens of red blood cells important in transfusion medicine, the CD antigens of T cells and the cancer antigens of malignant cells, for example. These reagents comprise, for example, the usual blood typing reagents of various specificities as used in blood bank laboratories but modified in accordance with the present invention. That is, they are tagged with magnetic particles or beads, so that red cells (or any other blood cells, such as white cells and platelets) coated with the magnetic capture reagents and sample antibody coated onto tagged reagent red cells can be moved as a complex in a magnetic field. In addition, novel magnetic tagged reagents comprising entities such as lectins, non-immunological binding pairs and universal binding agents which will bind to all blood cells, regardless of blood type, may also be used in the invention.

Such blood cells coated with these reagents can in some embodiments be captured by the magnetic field of the invention and held stationary rather than being moved, for reading or for further processing in the test such as washing, concentration, prolonging and enhancing antibody incubation and the like. For example, the magnetic field can hold the particles in place and the liquid zones moved past the stationary particles. If the magnetic field is removed, the cells will continue to flow with the liquid according to the individual test protocol.

The magnetic particle tagged reagents enable phenotyping of a vast range of cells for a vast range of phenotypes. Cells to which these magnetic reagents bind can be delivered by the magnetic field of the invention to a detector zone can indicate the presence of the specific antigens on the cell surface corresponding to the specific antibody of the tagged particle complex. Selected cells can be delivered to a harvest area where they can be subjected to further downstream processing such as cell culture or PCR.

There are many procedures that employ separation or segregation of cell populations of interest such as:

Sentinel Lymph Node Biopsy Application

In sentinel lymph node biopsy, a sample of lymph node is disaggregated into a small suspension volume. This is introduced into a well with three layer zones. The top zone contains magnetic particle tagged anti-epithelial cell antibody binds only to breast cancer cells. The lower separating liquid zone is an inert fluorochemical liquid of higher density or other dense liquid which separates the top layer from the culture layer zone which is made up of a living cell sustaining solution of even higher density than the separating layer. Alternatively, the culture zone can be of similar density as the sample but is separated from the sample zone by a baffle on the sides and the dense separating zone on the bottom. A magnet is applied to the bottom of the well which moves the magnetic particle tagged cancer cells selectively to the transparent bottom surface leaving all of the other lymph node cells floating in the top layer as they are unable to enter the denser separating layer. There they can be examined microscopically by a pathologist. Either the bottom layer or the top layer may also contain several varicolored immunohistochemical stains that bind to the cancer cells, allowing multiplex phenotyping of the cancer cells for her or other phenotypes. Following examination they are also available for cell culture by moving them to the culture zone or PCR molecular testing by moving them to an appropriate zone.

CD4 T Cell Levels in HIV Patients

Another embodiment of the invention concerns a simple measure of CD4 T cell levels in HIV patients suitable for use in the field. A measured blood or buffy coat sample from the patient is introduced into the top zone layer of a column which contains labeled-buoyant-mag-anti-CD4 antibody reagent. After time for specific reaction of antibody reagent with all and only CD4 T cells, a magnetic field is applied forcing just the mag-tagged CD4 T cells down through a denser layer which will reject all other T cells (and all other cells of any kind) to the transparent bottom surface of the vessel containing the continuous liquid column. The CD4 T cell count may be obtained by counting the CD4 T cells delivered to the bottom surface microscopically or measuring their label quantitatively with a densitometer.

CD4+/CD25+ T Reg Cells

This subset of T cells, CD4+/CD25+ T Reg Cells, has become very important in immunological research, in cancer therapy, diabetes, in autoimmune diseases and in organ transplantation. T Reg cells are essential for immunological tolerance to self. In cancer, they have been shown to infiltrate the tumor and block the body's natural anti-tumor immunity. It has been possible to cure Diabetes Type 1 in mice and efforts in human diabetes are being actively pursued showing the importance of these cells. 'Educating' the immune system to accept transplanted grafts as self is a formidable challenge that immunologists have been tackling for decades. Efforts are being made to manipulate T reg cell populations to allow transplantation without immunosuppresion. There is a need for better methods of detecting, isolating and counting these cells in many clinical situations. The invention envisages three methods of performing this assay which illustrate the great flexibility of the general method in providing opportunities for creating variations that achieve special purposes. First, using the method above to isolate CD4+ T cells, but incubating the buffy coat cells with binding mag.CD4 antibody and fluroescin labeled Cd-25 antibody. All CD4+ T cells will be forced to the bottom surface with the CD25+ subset identified for study by its flouorescin label. Second, using the same method to force all CD4+ cells to a bottom surface which in this case has attached anti-CD25 antibody. When the magnet is removed, flotation will remove all CD4+ cells not bound to the surface by the fixed anti-CD25 antibody leaving a pure subset of fluorescin CD4+ CD25+ T cells at the surface for study. Third, by incubating buffy coat cells with both mag-CD4 antibody tagged with small mag particles, and CD25 antibody tagged with larger mag particles, and providing two fluid separating zones, a less dense layer on top of a more dense layer. In this case, magnetic field strength is such as to force the CD4+ tagged T cells down into the first zone but not intense enough to force them into the denser zone. CD4+ CD25+ Tcells tagged with both mag-antibodies will be forced all the way to the bottom surface.

Molecule Separations

Molecule separations. It is sometimes desirable to purify materials by specifically binding material to a capture molecule, for example an antibody bound to a magnetic particle, and then removing the bound material from unbound material and finally releasing the bound material, regenerating the capture molecule. This can be done with a magnetic particle coupled to an antibody specific for a material to be purified. Consider a baffled container with a separating zone covering the bottom and part way up into each separate baffled zone, one of which contains material to be purified and the other of which contains a releasing chemical, for example, an acidic or basic or high salt solution. Mix the magnetic particles with the material to be purified and then force the particles through the separating zone and into the release zone. Mix in the release zone and then force the magnetic particles back through the separating zone and into the zone containing the material to be purified, mix and repeat this cycle as needed. At the end the purified material will be concentrated in the release zone and available for further processing.

Chemical Syntheses

As described in Example 8 above, the invention is directly applicable to chemical processes where it is necessary or desirable to provide separation steps between addition steps so that no materials involved in the previous step contaminate the next reaction.

In chemical synthesis the procedure involves:

1—providing a movable magnetic particle on which chemical synthesis can occur

2—in a plurality of separate chemical addition zones for different aspects of processing, (for example a bottomless microtiter plate placed into a layer of an inert solution or liquid, for example a fluorochemical, such that the bottom of each well is the fluorochemical) connecting with each other through the fluorochemical, move the particle by magnetic field from one zone to the next zone, through an inert layer selected (as a separate separating zone that will not mix or react with material in other zones or on the particle. The separate chemical zones can contain acids, bases, organic solvents, amino acids or other chemicals that are appropriate for the synthesis. The inert solution, for example a fluorochemical, is selected to be non-reactive with any reactants and preferably poorly miscible with the reactants, a liquid at the temperatures used in the process, typical examples could include perfluoro-n-octane, perflurodecalin, and perflurohexane among others. In a similar sense a less dense organic solvent could be selected that would float on top and be used as a cleaning zone.

3—The movement of the particle up, down or over through the addition and removal steps is done in the sequence needed to synthesize the desired material on the particle. There can be multiple types of cleaning zones in the same process, for example multiple reactant zones with a specific gravity between 1.0 and 1.4 and a more dense cleaning zone underneath consisting of a dense fluorocarbon (density 1.5 to 2.0) and a less dense organic solvent, for example acetone, floating on top of the multiple reactant zones.

What is claimed:

1. A method for detecting the presence or absence of an antigen on a blood cell in a liquid medium containing interfering proteins which comprises:

1. providing in a vessel:
    a) a continuous liquid medium comprising relative to a vertical plane at least two separate liquid zones of different densities, a first zone of which comprises a reaction incubation zone and comprises a first liquid and a second zone of which comprises a second liquid each of said first liquid and said second liquid being contiguous with the other, and an end reading zone present in said liquid medium at a point which permits performing Step 5 below,
    b) a blood cell sample suspected of having said antigen to be determined,
    c) an antibody specific for the antigen sought to be determined, and
    d) magnetic particle tagged moieties which are reactable with said blood cells, to form a movable complex therewith, the components b), c) and d), being present in said first zone,
    e) a free anti-human immune globulin (AHG), with an attached readable label, present in said second liquid zone, having a density greater than the density of the first zone said AHG being capable of reacting with c) above, wherein said liquid in said second zone has a buoyant effect on, and is repugnant to, the presence of interfering proteins, unreacted said magnetic particle tagged moieties and said blood cells, if any,
2. allowing a complex of b) and d) to form in a negative test and a complex of b), c) and d) to form in a positive test, all in said first liquid zone,
3. applying a magnetic field to the complexes formed in Step 2 to move them into the second, denser, liquid zone into contact with said AHG present therein, wherein said AHG attaches to the antibody c) of said complex b), c) and d) if said antibody is present, thereby forming a further AHG complex with b), c) and d) and thereafter moving the further AHG complex to the end reading zone,
4. removing the magnetic field from the further complex, whereby any b), d) complex that may have formed and any unreacted magnetic particles not bound to the AHG, are dislodged from said further AHG complex due to the repugnant nature and buoyant effect of said second zone liquid on said unreacted unbound magnetic particles,
5. observing the complexes in the reading zone for the presence or absence of the AHG attached label, a positive test for said antigen sought to be determined being indicated by the presence of the AHG label thereon.

2. The method according to claim 1 wherein the AHG is labeled with a readable enzyme.

3. The method according to claim 1 wherein the cell sample is human cells and the antigen sought is a human antigen.

4. The method according to claim 1 wherein the moiety in Step 1d) is a lectin.

5. The method according to claim 1 wherein the specific antibody employed in Step 1c) is Anti-A, Anti-B or Anti-D antibodies and the specific antigen sought is Group A, Group B or Group D, respectively.

6. The method according to claim 1 wherein the density of the second liquid is higher than the density of the complex lacking the antigen sought for in Step 1c).

7. The method according to claim 1 wherein the cell sample of Step 1b) is a donor's red blood cells, the antibody of Step 1c) is a patient's serum and the method is a crossmatch method.

8. The method according to claim 1 wherein the lowermost liquid is a perfluorochemical.

9. A method for detecting the presence or absence of an antibody in a blood cell in a liquid medium containing interfering proteins which comprises:
   1. providing in a vessel, a mixture of:
      a) a continuous liquid medium comprising relative to a vertical plane at least two separate liquid zones of different densities, a first zone of which comprises a reaction incubation zone and comprises a first liquid and a second zone of which comprises a second liquid each of said first liquid and said second liquid being contiguous with the other, and an end reading zone present in said liquid medium at a point which permits performing Step 5 below,
      b) blood cells having cell antigens thereon, and
      c) a sample suspected of comprising antibodies to said cell antigens, and
      d) magnetic particle tagged moieties which are reactable with said blood cells, to form a movable complex therewith, the components b), c) and d) being present in said first zone,
      e) a free anti-human immune globulin (AHG), with an attached readable label, present in said second liquid zone having a density greater than the density of the first zone, said AHG being capable of reacting with c) above if antibodies are present in said sample, wherein said liquid in said second zone has a buoyant effect on, and is repugnant to, the presence of interfering proteins, unreacted said magnetic particle tagged moieties, and unreacted blood cells,
   2. allowing a complex of b) and d) to form in a negative test and a complex of b), c) and d) to form in a positive test, all in said first liquid zone,
   3. applying a magnetic field to the complexes formed in Step 2 to move them into the second, denser, liquid zone into contact with said AHG present therein, wherein said AHG attaches to the antibody c) of said complex b), c) and d) if said antibody is present, thereby forming a further AHG complex with b), c) and d), and thereafter moving the further AHG complex to the end reading zone,
   4. removing the magnetic field from the further complex, whereby any b), d) complex that may have formed and any unreacted magnetic particles not bound to the AHG, are dislodged from said further AHG complex due to the repugnant nature and buoyant effect of said second zone liquid on said unreacted unbound magnetic particles,
   5. observing the complexes in the end reading zone for the presence or absence of the AHG attached label, a positive test for said antigen sought to be determined being indicated by the presence of the AHG label thereon.

10. The method according to claim 9 wherein the blood cells in Step 1b) and in Step 1c) are of human origin, and the blood cells in Step 1b) are red blood cells.

11. The method according to claim 9 wherein the moiety in Step 1d) is a lectin.

12. The method according to claim 9 wherein the specific cells employed are group A, group B and group RhD respectively and the specific antibodies sought in Step 1c) are Anti-A, Anti-B or Anti-D antibodies.

13. The method according to claim 9 wherein the specific cells employed are group O red cells phenotyped for multiple red cell antigens and suitable for use in antibody screening and antibody identification, and the specific antibodies sought in Step 1c) are unexpected red cell antibodies.

14. The method according to claim 9 wherein the density of the second liquid is higher than the density of the complex lacking the antibody sought for in Step 1c).

15. The method according to claim 9 wherein the cell sample of Step 1b) is a donor's red blood cells, the antibody of Step 1c) is a patient's serum and the method is a crossmatch method.

16. The method according to claim 9 wherein the lowermost liquid is a perfluorochemical.

17. A method for detecting the presence or absence of an antibody in a liquid medium which contains interfering proteins which comprises:
   1. providing in a vessel, a mixture of :
      a) a continuous liquid medium comprising at least two separate liquid zones, a first zone of which constitutes a reaction incubation zone and comprises a first liquid and a second zone of which comprises a second liquid, each of first liquid and said second liquid being contiguous with the other, and an end reading zone present in said liquid medium at a point which permits performing Step 5 below,
      b) in said first zone, a sample suspected of containing said antibody to be determined, and magnetic particle tagged moieties comprising an antigen specific for the antibody sought to be determined capable of forming a first complex therewith if said antibody is present,
      c) a free anti-human immune globulin (AHG), with an attached readable label, present in said second liquid zone, having a density greater than the density of the first zon; said AHG being capable of reacting with antibody b), above, wherein said liquid in said second zone has a buoyant effect on, and is repugnant to, the presence of interfering proteins, unreacted said magnetic particle tagged moieties and blood cells present in said first zone, if any.
   2. allowing said sample and said magnetic particle tagged moieties in b) above to form a reaction mixture comprising said first complex in said first zone, if said antibody is present, and unreacted magnetic particles, if any, in said first zone,
   3. applying a magnetic field to the complexes formed in Step 2 to move them into the second, denser, liquid zone into contact with said AHG present therein, wherein said AHG attaches to the antibody of said first complex, if said antibody is present, thereby forming a further AHG complex with b), and thereafter moving the further AHG complex to the end reading zone,
4. removing the magnetic field from the further complex whereby any unreacted magnetic particles not bound to the AHG are dislodged from said AHG present in said second liquid zone due to the repugnant nature and buoyant effect of said second zone liquid on said unreacted unbound magnetic particles.
5. observing the complexes in the end reading zone for the presence or absence of the AHG attached label, a positive test for said antigen sought to be determined being indicated by the presence of the AHG label thereon.

18. The method according to claim 17 wherein the antibody sought is a member of the group consisting of antibody to toxoplasma, rubella, cytomegalovirus, herpes, hepatitis and HW.

19. The method according to claim 17 wherein the sample of Step 1b) is of human origin.

20. The method according to claim 17 wherein the second liquid zone has a density higher than unreacted reagent of Step 1c), and the lowermost liquid is a perfluorochemical.

\* \* \* \* \*